United States Patent [19]

Puig

[11] Patent Number: 4,995,876
[45] Date of Patent: Feb. 26, 1991

[54] NEUROSURGICAL CLIP APPLIER

[76] Inventor: Ana E. Puig, 308 Hawkeye Court, Iowa City, Iowa 52240

[21] Appl. No.: 826,911

[22] Filed: Feb. 6, 1986

Related U.S. Application Data

[63] Continuation-in-part of Ser. No. 716,496, Mar. 27, 1985, abandoned.

[51] Int. Cl.$^5$ ............................................. A61B 17/00
[52] U.S. Cl. ............................. 606/142; 227/901 LM
[58] Field of Search ............... 128/325, 321, 346, 354, 128/334 R; 606/142, 143; 227/DIG. 1

[56] References Cited

U.S. PATENT DOCUMENTS

| | | | |
|---|---|---|---|
| 1,496,132 | 6/1924 | Rombough | 128/321 |
| 3,828,791 | 8/1974 | Santos | 128/321 |
| 3,958,576 | 5/1976 | Komiya. | |
| 4,169,476 | 10/1979 | Hiltebrandt. | |
| 4,241,734 | 12/1980 | Kandel et al. | |
| 4,242,902 | 1/1981 | Green. | |
| 4,246,903 | 1/1981 | Larkin. | |
| 4,367,746 | 1/1983 | Derechinsky. | |
| 4,448,194 | 5/1984 | DiGiovanni et al. | 128/334 R |
| 4,462,404 | 7/1984 | Schwarz et al. | 128/354 |
| 4,562,839 | 1/1986 | Blake, III et al. | 128/334 R |
| 4,602,631 | 7/1986 | Funatsu | 128/325 |

Primary Examiner—C. Fred Rosenbaum
Assistant Examiner—Kathleen A. Daley
Attorney, Agent, or Firm—Saliwanchik and Saliwanchik

[57] ABSTRACT

A surgical instrument for applying ligating clips. The instrument is made with as few detachable parts as possible to avoid any possibility that parts may be loosened and fall into the body of the person being operated on. To this end the instrument has a pair of jaws made from one piece of material or permanently joined to each other and a pair of handles which are similarly constructed. When the handles are pivoted toward each other, the motion is converted by a cam and roller or by elastic deformation of a spring member to linear motion of a push rod which impinges on and forces one of the jaw members toward engagement with the other jaw member, thereby squeezing and applying a ligating clip to a blood vessel or to other tissue.

6 Claims, 2 Drawing Sheets

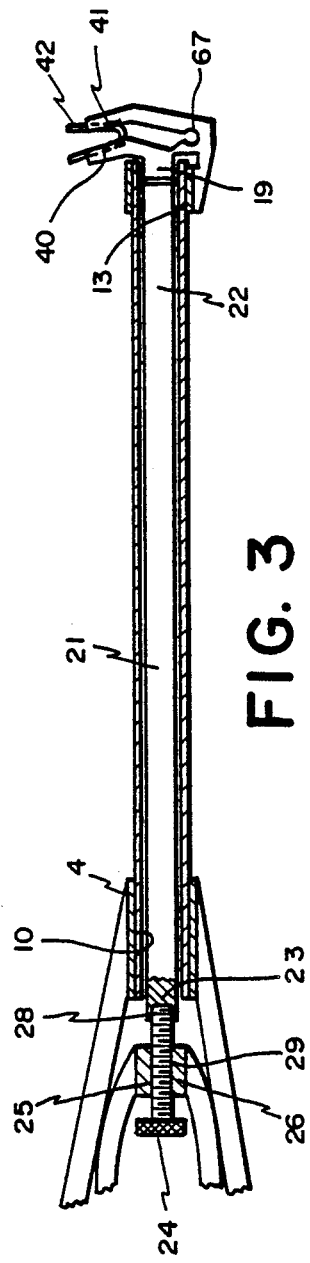
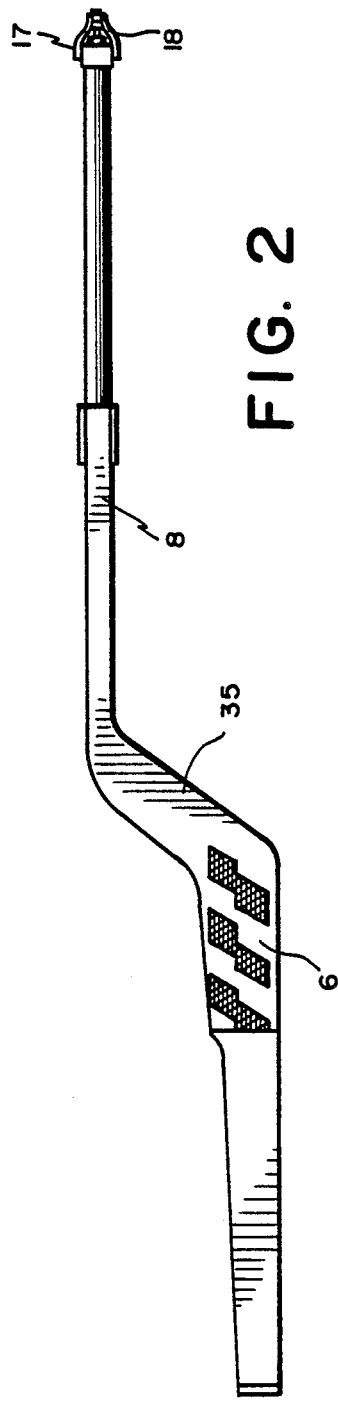
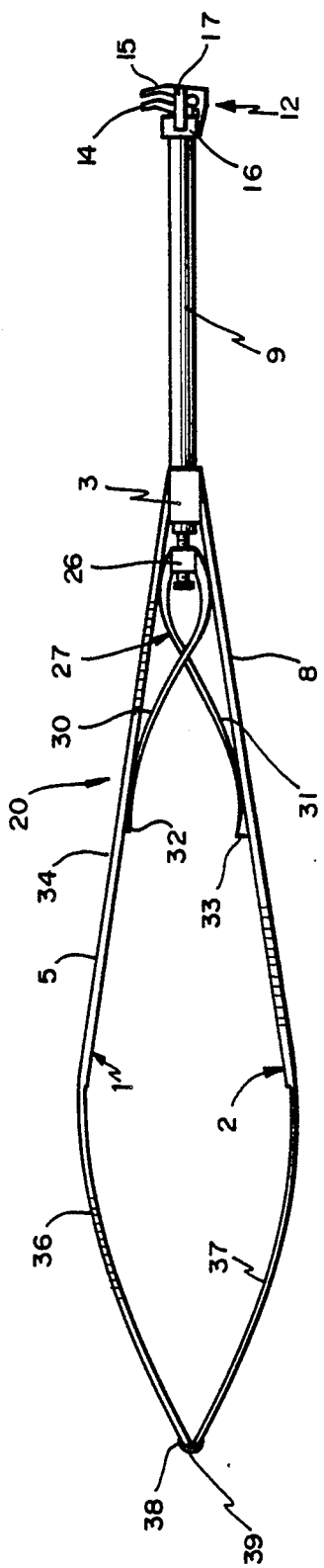

NEUROSURGICAL CLIP APPLIER

BACKGROUND OF THE INVENTION

This application is a continuation in part of my copending application Ser. No. 716496, filed Mar. 27, 1985, now abandoned.

This invention relates to the field of surgery and surgical instruments and is more particularly concerned with a surgical instrument for applying hemostatic or ligating clips to blood vessels and to tissue during operations in the human body. The instrument is particularly adapted for use in neurosurgical operations and other surgical procedures in confined and critical areas of the body.

It is well known to use hemostatic or ligating clips in the course of surgical operations. Various forms and shapes of such clips are also well known. Generally the clips have a bight portion and an open end so the clip can be applied over a the blood vessel or tissue and then clamped thereon. The clips are constructed with latching means or of materials which will cause the clip to remain in its clamped condition after release of the instrument by which they were clamped. The invention is illustrated and described as applied to a V-shaped clip but it is obvious that any person skilled in the art could make minor modifications to the jaws as shown to adapt the instrument to substantially any size or configuration of clip now known or to be devised.

Clip appliers of the prior art often have magazines for storing extra clips which makes them bulky and difficult to use in restricted places such as are encountered in neurosurgery, have the distal clip applying end in line with the magazine and the other operating portions of the instrument which makes it difficult to observe visually the position and application of the clip, are operated by scissor like handles which require the insertion of the thumb and fingers making it more difficult to grasp and hold the instrument and have complicated pivot and lever motions which require a multiplicity of parts and increase the possibility that small parts may break or come loose and fall into the body of the person being operated on.

The instrument of this invention avoids the disadvantages described above and provides many other advantages which will hereinafter be explained.

SUMMARY OF THE INVENTION

A preferred embodiment of this invention provides a clip applier in which the clip is held and applied by a pair of movable jaws in confronting relationship with each other which are formed of a single piece of material to avoid the potential loss or breakage of small parts and bulkiness of pivots or other mechanisms. Movement of one jaw toward the other takes place through elastic flexing of the material of which the jaws are formed at the junction between them. A pair of rigid handles are formed integrally with each other and are joined together at a junction or bight portion. The handles can be squeezed toward each other by elastic flexing of the material of which they are made at or near the junction or bight portion. The handles are shaped to fix comfortably in the fingers or palm of the hand and are squeezed together by closing the fingers or hand about them. The inward pivotal motion of the handles is converted to linear motion by a generally V-shaped spring member having a bight portion and a pair of longitudinally extending leg portions. The leg portions have free ends spaced apart from each other and rigidly secured to the adjacent point of the handles so that when the handles are squeezed together moving the leg portions with them, the bight portion of the spring members will move longitudinally away from the point of attachment between the handles and the leg members. The inward end of the handles is connected by a rigid tubular member to the head of the instrument which includes the jaws and a rigid actuating rod or pushrod is arranged for reciprocating movement within the tubular member. The actuating rod has one end connected to the bight portion of the spring member and has its other end abutting one of the jaws so that when the handles are squeezed and the bight portion of the spring member moves longitudinally the actuating rod is also moved longitudinally in a direction to force the one jaw toward the other compressing and closing a clip held there between. Alternatively a cam and roller or other mechanical arrangement may be used to convert pivotal movement of the handles to linear motion of the pushrod. The jaws and handles are rotatable with respect to each other about the axis of the pushrod to increase the versatility of the instrument. Several alternative arrangements to provide such rotation are shown.

The invention is illustrated and described as an instrument for applying hemostatic or ligating clips during the performance of neurosurgical operations. It is obvious that an instrument made in accordance with the teachings of the invention can be made to handle various other types of clips which can be used in other surgical and non-surgical applications.

It is an object of this invention to provide a surgical instrument for use as a clip applier in critical and confined parts of the human body.

Another object of this invention is to provide a clip applier that can be comfortably grasped and operated.

Another object of this invention is to provide a clip applying instrument for use in neurosurgical procedures which will provide improved visibility of the clip and the body tissue to which it is being applied.

A further object of this invention is to provide a clip applier for use in neurosurgical operations which has a rotating head and handles so that clips may be applied at substantially any angle and in any direction of rotation.

It is also an object of this invention to provide a clip applier for use in surgical operations which is compact, of simple construction and easy to use in confined applications.

These and other objects, features, and advantages of this invention will become apparent from the following description in conjunction with the accompanying drawings.

BRIEF DESCRIPTION OF THE DRAWINGS

FIG. 1 is a plan view of a first embodiment of the invention.

FIG. 2 is a side view of the instrument shown in FIG. 1.

FIG. 3 is an enlarged view partly in cross section of a portion of FIG. 1.

DETAILED DESCRIPTION OF THE INVENTION

Figure 5:
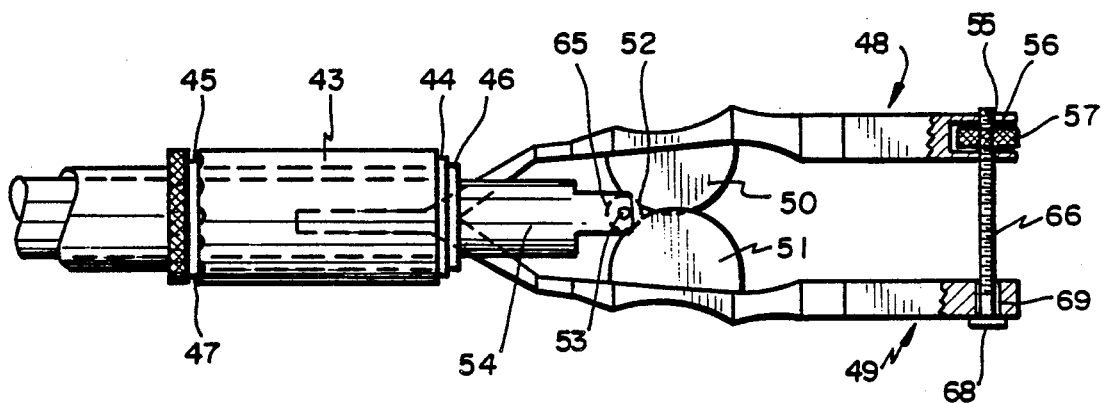
FIG. 5 shows an alternative form of the invention.

Turning to FIG. 1 it can be seen that the instrument 20 comprises a pair of handles 1 and 2 which are integrally formed with or permanently connected to a connection block 3 which may be internally threaded as indicated at 4 in FIG. 3. The handles 1 and 2 are relatively rigid but can be moved toward each other by applying pressure to the distal portions 5 and 6 to cause elastic deformation of the handle material in the inward portions 7 and 8. A rigid tubular member 9 is attached to the connection block 3 as by threads 10 as shown in FIG. 3. The distal end 11 of tubular member 9 is connected to a head 12 by threads 13 or other suitable means. Head 12 comprises an inner or movable jaw 14 and an outer jaw or anvil 15 integrally formed with each other and with an attaching hub 16. As previously indicated the hub 16 may be connected to the distal end of the tubular member 9 by threads 13 or other suitable attaching means. Reinforcing plates 17 and 18 are provided to rigidly and permanently connect the anvil 15 to hub 16 and to prevent movement of the anvil member with respect to the hub and the tubular member 9. Movable jaw 14 has an abutment member 19 integrally formed therewith and extending into the distal end of tubular member 9 as best seen in FIG. 3. A rigid actuating rod or pushrod 21 is mounted for reciprocating motion within the tubular member 9 and has its distal end 22 abutting the abutment member 19 and its opposite or inner end 23 extending through connection block 3. The inner end of pushrod 21 is provided with a socket 28 to receive the end 64 of adjusting screw 24. End 64 of the adjusting screw is preferably unthreaded. The threaded stem portion 25 of the adjusting screw is threadedly engaged with the drive block or bight portion 26 of spring member 27. Spring member 27 has legs 30 and 31 which have their free ends 32 and 33 respectively rigidly and permanently connected to handles 1 and 2 as may be seen in FIG. 2. The inward portions 7 and 8 of handles 1 and 2 respectively are offset from rigid distal portions 5 and 6 of handles 1 and 2 by intermediate rigid portions 34 and 35 respectively.

When handles 1 and 2 are moved toward each other, legs 30 and 31 of spring member 27 will also move toward each other forcing drive block 26 to move linearly in a direction toward the head 12. This will cause the pushrod 21 to push against abutment number 19 of the movable jaw 14 moving it toward engagement with anvil member 15. The junction between the jaws is provided with a substantially circular notch 67 which facilitates the necessary resilient bending. When the handles are released they will start to move toward their initial position due to the elasticity of portions 7 and 8 thereof and legs 30 and 31 of spring member 27 will tend to return elastically to their original position helping to move the handles apart from each other. The handles 1 and 2 respectively have spring extensions 35 and 36 integrally formed therewith or rigidly secured thereto to further assist the return action. The distal end 38 of spring extension 36 is loosely confined by hook or retaining loop 39 on the distal end of spring extension 37 of handle 2. Spring portions 36 and 37 are shown as extending longitudinally in the same direction as portions 5 and 6 of handles 1 and 2 to aid in the balance of the tool. Push rod 21 may be made hollow to reduce weight at the heel end and improve balance of the instrument. Other forms and shapes (not shown) of spring members may be utilized including a compression coil spring or a U-shaped flat spring located between the distal portions 5 and 6 of the handles. The jaws 14 and 15 are each provided with a groove or depression 40 and 41 respectively to receive a ligating clip 42 or the like and help hold it between the jaws preparatory to its being applied surgically. The opposed surfaces of the jaws may be serrated or otherwise treated to further assist in retaining the clip.

Figure 4:
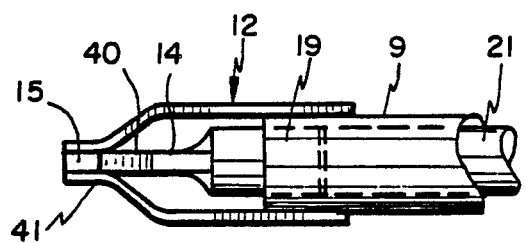
FIG. 4 is an enlargement of the head portion of a modified embodiment of the invention.

To permit better maneuverability and visibility of the jaws of the instrument when it is being used to apply a clip, head 12 may be rotated on the threads 13 with respect to tubular member 9 and/or the tubular member 9 may be rotated about its axis within the threaded portion of connection block 3. To avoid the possibility of head 12 becoming disengaged from the instrument head 12 may be formed integrally with tubular member 9 or welded or otherwise rigidly and permanently secured thereto as indicated in FIG. 4. Relative rotation of the parts can then be accomplished at connection block 3.

To apply a clip 42 to a blood vessel for example, adjusting screw 24 is rotated until the distal end 22 of pushrod 21 engages the abutment 19 of jaw 14 and the opening between jaws 14 and 15 is of a size to yieldingly engage a clip 42 and hold it while it is being moved into position to be applied. A clip is then inserted between the jaws with the bight portion of the clip extending inwardly, as shown in FIG. 3, and the clip is moved into position about the blood vessel with the instrument. When the clip is in proper position, the handles 1 and 2 are squeezed together compressing the legs of spring 27 and causing it to elongate. This causes pushrod 21 to move longitudinally against abutment 19 of jaw 14 forcing jaw 14 forward toward anvil 15 which is held against movement by reinforcing plates 17 and 18. This motion of jaw 14 toward anvil 15 deforms the clip 42 until it is clamped in position on the blood vessel shutting off the flow of blood. Handles 1 and 2 are then released and the resilience of spring members 27, 36 and 37, and the resilience of the jaws themselves causes the handles, springs and jaw members all to return to their initial positions.

It should be understood that the instrument is made so that it is comfortable and balanced when held in the hand. To achieve these conditions, the size and thickness of the handle portions are selected to achieve a balance between the handles and the head end of the instrument when it is held with the fingers and thumb in the manner in which it would be most conveniently held to apply surgical clips. Surgical grade steel or stainless steel or other materials suitable for the application for which the instrument is designed are utilized and it is important that the material selected have a modulus of elasticity that will permit the bending and flexing indicated in the description without causing any residual permanent deformation.

Figure 7:
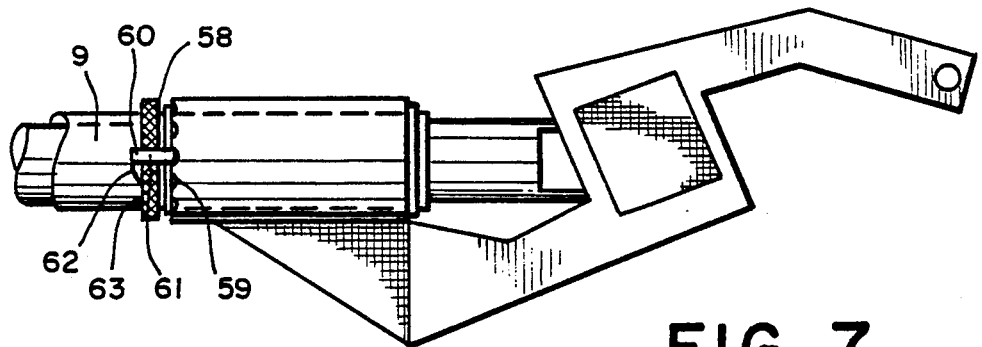
FIG. 7 shows details of a mechanism for providing rotary adjustment between the head of the instrument and the handles thereof.
Figure 6:
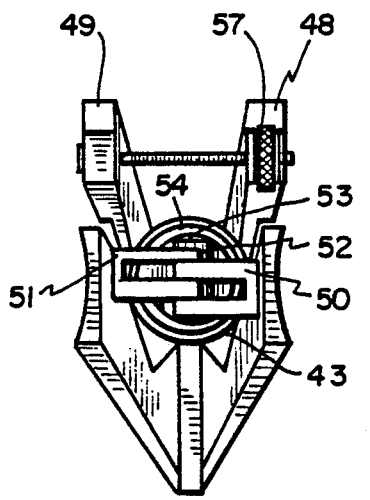
FIG. 6 is a detailed view of the cam and roller of the form of the invention shown in FIG. 5.

FIG. 5 shows an alternate arrangement for permitting rotation of the handles of the instrument with respect to the tubular member 9 and also shows alternative cam and roller means for converting pivoting motion of the handles into linear reciprocating motion of the pushrod 21. As will best be seen in FIG. 7, rotation and retention of the tubular member with respect to the handles is accomplished by means comprising a sleeve 43 freely rotatable on the tubular member 9 but held against longitudinal motion thereon by spring retaining rings 44 and 45 which fit into complimentary grooves 46 and 47 on the tubular member 9 adjacent each end of the sleeve. Sleeve 43 is comparable to connection block 3 of FIG. 1 and handles 48 and 49 are permanently secured thereto. Handles 48 and 49 are in opposed relation to each other and may be pivoted toward each other by elastic bending or flexing of the material of which they are made adjacent to the point of attachment to the sleeve 43. Handles 48 and 49 have cam lobes 50 and 51 formed on their inner surfaces and in contact with a cam roller 52. Cam roller 52 is mounted for rotation on pivot pin or axle 53 which is secured in apertures 65 in the end of a pushrod 54. When handles 48 and 49 are squeezed together, cam roller 52 will roll along the edges of cam lobes 50 and 51 and be forced to move along the axis of pushrod 54 carrying pushrod 54 with it. Linear motion of pushrod 54 will cause jaw 14 to move toward jaw 15 as previously described in connection with FIG. 3.

Handle 48 may be provided with a bifurcated portion adjacent its distal end to hold an internally threaded nut 57 which is threaded onto the stem 56 of an adjusting screw 68. The nut 57 may be knurled to facilitate manipulation of the nut. Screw 56 is held against rotation in handle 49 but is free to slide longitudinally through a bore 69 therein. Rotation of the nut 57 will determine the initial position of the handles relative to each other and the initial opening between the jaws 14 and 15. A compression coil spring 66 may be provided to urge the handles toward their open position.

Alternative means for adjusting the relative rotational position of the handles with respect to the head may also be provided. An example of one such adjusting system is indicated in detail in FIG. 7 in which an adjusting ring 58 is integrally formed or welded or otherwise permanently secured to tubular member 9 adjacent to sleeve 43. Sleeve 43 is provided with a series of spaced substantially hemispherical notches 59 along its adjacent circumferential edge and adjusting ring 58 is provided with one or more locking detents 60 which are in registry with and selectively engage the notches. The detents 60 are reciprocable within suitable bores 61 in the locking ring and are biased into engagement with the notches by leaf springs 62 or other suitable biasing device. Springs 62 are secured by rivets 63 or other suitable means to the adjusting ring 58 and serve to releasably hold the detents in the notches. Step by step adjustment of the relative rotational position of the head and handles may be made by turning the adjusting ring while holding the handles. This will force the detents 60 to move out of the notches 59 against the bias of springs 62 until they reach the next notch and so on until the desired position is reached.

It is obvious to those skill in the art that although the invention has been shown and described in a limited number of preferred embodiments, many variations may be made in the form and structure here presented without departing form the scope of the present invention as set forth in the appended claims.

What is claimed is:

1. A surgical instrument for applying surgical ligating clips onto a blood vessel or tissue in connection with a surgical operation, said instrument comprising a pair of opposed jaws integrally joined to each other but capable of pivoting movement toward and away from each other by elastic bending of the material from which they are formed, a pair of opposed handles integrally joined to each other but capable of pivoting movement toward and away from each other by elastic bending of the material from which they are formed, and actuating member comprising a pair of leg members joined together by a bight portion, the free ends of each of said leg members being rigidly secured to a respective one of said opposed handles, a push rod connecting said bight portion to one of said pair of opposed jaws, said leg members and said bight portion being integrally joined to each other so that no relative motion between the bight portion and either of said leg members is possible at the point of juncture between them whereby pivoting movement of said handles is converted into linear reciprocating movement of said bight portion and of said push rod thereby causing pivoting motion of said one of said pair of opposed jaws.

2. A surgical instrument for applying surgical ligating clips onto a blood vessel or tissue in connection with a surgical operation, said instrument comprising a pair of opposed jaws integrally joined to each other so that no relative motion between them is possible at the point of juncture but capable of pivoting movement toward and away from each other by elastic bending of the material from which they are formed, a pair of opposed handles integrally joined to each other but capable of pivoting movement toward and away from each other by elastic bending of the material from which they are formed, an actuating member, first means comprising a cam and roller for converting pivoting movement of the handles into linear reciprocating motion of said actuating member, further means interposed between said actuating member and one of the jaws for converting, reciprocating motion of the actuating member into pivoting motion of one of said jaws toward the other of said jaws whereby said jaws are movable from a first position in which they will receive and retain therebetween an open ligating clip and a second position in which the clip is clamped onto a blood vessel or tissue.

3. A surgical instrument for applying surgical ligating clips onto a blood vessel or tissue in connection with a surgical operation, said instrument comprising a pair of opposed jaws integrally joined to each other so that no relative motion between them is possible at the point of juncture but capable of pivoting movement toward and away from each other by elastic bending of the material from which they are formed, a pair of opposed handles integrally joined to each other but capable of pivoting movement toward and away from each other by elastic bending of the material from which they are formed, an actuating member, first means comprising a cam and roller for converting pivoting movement of the handles into linear reciprocating motion of said actuating member, further means interposed between said actuating member and one of the jaws for converting, reciprocating motion of the actuating member into pivoting motion of one of said jaws toward the other of said jaws whereby said jaws are movable from a first position in which they will receive and retain therebetween an open ligating clip and a second position in which the clip is clamped onto a blood vessel or tissue; said instrument further comprising a rigid tubular member interconnecting said jaws and said handles; and wherein said actuating member is a rigid elongated rod mounted for reciprocating movement with said right tubular member.

4. A surgical instrument for applying surgical ligating clips onto a blood vessel or tissue in connection with a surgical operation, said instrument comprising a pair of opposed jaws integrally joined to each other so that no relative motion between them is possible at the point of juncture but capable of pivoting movement toward and away from each other by elastic bending of the material from which they are formed, a pair of opposed handles integrally joined to each other but capable of pivoting movement toward and away from each other by elastic bending of the material from which they are formed, an actuating member, first means comprising a spring means for converting pivoting movement of the handles into linear reciprocating motion of said actuating member, further means interposed between said actuating member and one of the jaws for converting, reciprocating motion of the actuating member into pivoting motion of one of said jaws toward the other of said jaws whereby said jaws are movable from a first position in which they will receive and retain therebetween an open ligating clip and a second position in which the clip is clamped onto a blood vessel or tissue; said instrument further comprising a rigid tubular member interconnecting said jaws and said handles; and wherein said actuating member is a rigid elongated rod mounted for reciprocating movement within said rigid tubular member.

5. A surgical instrument for applying surgical ligating clips onto a blood vessel or tissue in connection with a surgical operation, said instrument comprising a pair of opposed jaws integrally joined to each other so that no relative motion between them is possible at the point of juncture but capable of pivoting movement toward and away from each other by elastic bending of the material from which they are formed, a pair of opposed handles integrally joined to each other but capable of pivoting movement toward and away from each other by elastic bending of the material from which they are formed, an actuating member, first means for converting pivoting movement of the handles into linear reciprocating motion of said actuating member, further means interposed between said actuating member and one of the jaws for converting, reciprocating motion of the actuating member into pivoting motion of one of said jaws toward the other of said jaws whereby said jaws are movable from a first position in which they will receive and retain therebetween an open ligating clip and a second position in which the clip is clamped onto a blood vessel or tissue, said opposed jaws in the first position define an initial opening therebetween and said instrument is further characterized by adjusting means connected between said first means and said actuating member, said adjusting means being effective to control the size of said initial opening; said instrument further comprising a rigid tubular member interconnecting said jaws and said handles; and wherein said actuating member is a rigid elongated rod mounted for reciprocating movement within said rigid tubular member.

6. A surgical instrument for applying surgical ligating clips onto a blood vessel or tissue in connection with a surgical operation, said instrument comprising a pair of opposed jaws integrally joined to each other so that no relative motion between them is possible at the point of juncture but capable of pivoting movement toward and away from each other by elastic bending of the material from which they are formed, a pair of opposed handles integrally joined to each other but capable of pivoting movement toward and away from each other by elastic bending of the material from which they are formed, an actuating member, first means for converting pivoting movement of the handles into linear reciprocating motion of said actuating member, further means interposed between said actuating member and one of the jaws for converting, reciprocating motion of the actuating member into pivoting motion of one of said jaws toward the other of said jaws whereby said jaws are movable from a first position in which they will receive and retain therebetween an open ligating clip and a second position in which the clip is clamped onto a blood vessel or tissue, said opposed jaws in the first position define an initial opening therebetween and said instrument is further characterized by adjusting means connected between the handles, said adjusting means being effective to control the size of said initial opening; said instrument further comprising a rigid tubular member interconnecting said jaws and said handles; and wherein said actuating member is a rigid elongated rod mounted for reciprocating movement within said rigid tubular member.

* * * * *

UNITED STATES PATENT AND TRADEMARK OFFICE
CERTIFICATE OF CORRECTION

PATENT NO.　　:　　4,995,876

DATED　　　　:　　February 26, 1991

INVENTOR(S)　:　　Ana E. Puig

It is certified that error appears in the above-identified patent and that said Letters Patent is hereby corrected as shown below:

Column 6, line 64 (claim 3): "movement with" should read --movement within--.
Column 6, line 64, "right" should read --rigid--.

Signed and Sealed this

Twenty-ninth Day of September, 1992

*Attest:*

DOUGLAS B. COMER

*Attesting Officer*　　　　*Acting Commissioner of Patents and Trademarks*